United States Patent
Chung et al.

(10) Patent No.: US 9,826,895 B2
(45) Date of Patent: Nov. 28, 2017

(54) ENDOSCOPE WITH SINGLE COOLING MEDIUM TUBE INTRODUCING OR DISCHARGING COOLING MEDIUM

(71) Applicant: Samsung Electronics Co., Ltd., Gyeonggi-do (KR)

(72) Inventors: Hae-In Chung, Gyeonggi-do (KR); Mun-Kue Park, Gyeonggi-do (KR); Jin-Won Lee, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 373 days.

(21) Appl. No.: 13/790,741

(22) Filed: Mar. 8, 2013

(65) Prior Publication Data
US 2014/0142384 A1   May 22, 2014

(30) Foreign Application Priority Data
Nov. 22, 2012   (KR) .................. 10-2012-0133099

(51) Int. Cl.
| | |
|---|---|
| *A61B 1/00* | (2006.01) |
| *A61B 1/12* | (2006.01) |
| *A61B 1/06* | (2006.01) |
| *A61B 1/008* | (2006.01) |
| *A61B 1/005* | (2006.01) |

(52) U.S. Cl.
CPC ............ *A61B 1/128* (2013.01); *A61B 1/0008* (2013.01); *A61B 1/0676* (2013.01); *A61B 1/005* (2013.01); *A61B 1/008* (2013.01); *A61B 1/12* (2013.01)

(58) Field of Classification Search
CPC ... A61B 1/0661; A61B 1/0669; A61B 1/0684; A61B 1/0692; A61B 1/0119; A61B 1/005; A61B 1/008; A61B 1/12; A61B 1/128

USPC .................. 600/156, 158, 159, 178–179
See application file for complete search history.

(56) References Cited

U.S. PATENT DOCUMENTS

| | | | | |
|---|---|---|---|---|
| 6,480,389 | B1* | 11/2002 | Shie et al. ................... | 361/707 |
| 7,914,448 | B2 | 3/2011 | Bob et al. | |
| 2003/0163025 | A1* | 8/2003 | Kaji .............................. | 600/132 |
| 2005/0075538 | A1* | 4/2005 | Banik et al. ................. | 600/141 |
| 2006/0173244 | A1* | 8/2006 | Boulais et al. .............. | 600/156 |
| 2007/0247867 | A1* | 10/2007 | Hunter et al. ............... | 362/551 |
| 2008/0009677 | A1* | 1/2008 | Shoroji et al. .............. | 600/160 |
| 2008/0239070 | A1* | 10/2008 | Westwick et al. .......... | 348/68 |
| 2008/0242927 | A1* | 10/2008 | Hirata .......................... | 600/109 |

(Continued)

FOREIGN PATENT DOCUMENTS

| | | |
|---|---|---|
| JP | 2002291693 | 10/2002 |
| JP | 2007007321 | 1/2007 |

*Primary Examiner* — John P Leubecker
*Assistant Examiner* — Arnaldo Torres Diaz
(74) *Attorney, Agent, or Firm* — The Farrell Law Firm, P.C.

(57) ABSTRACT

An endoscope is provided and includes a flexible insertion tube; a distal end assembly provided at an end of the insertion tube; and a cooling medium tube provided in the inside of the insertion tube, and connected to the distal end assembly. A cooling medium for cooling the distal end assembly is introduced through one of the insertion tube and the cooling medium tube, and discharged through the other of the insertion tube and the cooling medium tube. Since the endoscope is configured such that the cooling medium directly contacts with a heating element or a conductor through which the heat of the heating element is conducted, the cooling effect of the front end portion of the endoscope is improved.

14 Claims, 10 Drawing Sheets

(56) References Cited

U.S. PATENT DOCUMENTS

| | | | |
|---|---|---|---|
| 2009/0076328 A1* | 3/2009 | Root et al. | 600/131 |
| 2009/0315986 A1* | 12/2009 | Ohara | 348/65 |
| 2010/0048999 A1* | 2/2010 | Boulais | A61B 1/00059 600/141 |
| 2010/0087712 A1* | 4/2010 | Ito | A61B 1/0008 600/160 |
| 2010/0137847 A1* | 6/2010 | Cecchetti et al. | 606/2.5 |
| 2010/0177519 A1* | 7/2010 | Schlitz | 362/294 |
| 2010/0317922 A1 | 12/2010 | Kumai | |
| 2011/0092772 A1 | 4/2011 | Weber et al. | |
| 2011/0295072 A1* | 12/2011 | Boulais et al. | 600/176 |
| 2011/0306834 A1* | 12/2011 | Schrader et al. | 600/112 |
| 2012/0035419 A1* | 2/2012 | Ashida et al. | 600/109 |
| 2012/0051059 A1* | 3/2012 | Nakabayashi et al. | 362/294 |
| 2013/0131451 A1* | 5/2013 | Dillinger et al. | 600/127 |

\* cited by examiner

ENDOSCOPE WITH SINGLE COOLING MEDIUM TUBE INTRODUCING OR DISCHARGING COOLING MEDIUM

PRIORITY

This application claims priority under 35 U.S.C. §119(a) to Korean Application Serial No. 10-2012-0133099, which was filed in the Korean Intellectual Property Office on Nov. 22, 2012, the entire content of which is incorporated herein by reference.

BACKGROUND OF THE INVENTION

1. Field of the Invention

The present invention generally relates to an endoscope, and more particularly, to a heat radiation structure at the front end portion of the endoscope.

2. Description of the Related Art

Due to the introduction of medical endoscopes, the early detection rate of a disease is enhanced. Furthermore, as an endoscopy operation is made feasible, it becomes possible to prevent a side effect caused by an open abdominal operation or the like. Accordingly, the use of endoscopes has gradually increased in the medical field. In addition, as the size of endoscopes has been reduced and narrowed in order to lessen patients' pains, demands for an endoscope with a high resolution image sensor have also increased. Furthermore, it is obvious that a sufficient amount of light should be provided through an illumination device in order to satisfy the high resolution of an image sensor.

Two types of illumination for an endoscope are typically provided. The first type of illumination is to position a light source in an endoscope equipment body side, in other words, outside of a patient, and to arrange a light wave guide, such as an optical fiber, within an insertion tube to transmit light to the front end portion of the endoscope. In such a case, a lens may be mounted on the front end portion of the endoscope. The second type of illumination is configured such that a light source is directly mounted on the front end portion of the endoscope, in which case a power line connected to the light source should be provided in place of the light wave guide. That is, in the second type of illumination, the light source is inserted into the inside of the patient's body.

In the first type of illumination, it is not required to take heating by the light source into consideration because the light source is positioned outside of the patient's body. However, in the second type of illumination, because the light source is inserted into the patient's body, damage to a human anatomy by the heating of the light source or the like must be taken into consideration. Meanwhile, in the first type of illumination, the light should be transmitted through the light wave guide over a considerable length, and the light wave guide is curved many times inside of the patient's body. Accordingly, it is unavoidable that light is lost while the light is progressing in the light wave guide, and hence there is a limit in providing sufficient illumination for securing a high resolution image. The second type of illumination allows light produced from the light source to be used without loss because the light source is directly mounted on the front end portion of the endoscope. Accordingly, as the resolution of the image sensor of the endoscope is increased, the second type of illumination becomes more useful. However, as described above, with the second type of illumination, damage to the human anatomy caused by heating of the light source should be prevented. Therefore, the second type of illumination is preferably provided with a heat radiating and/or cooling structure in the front end portion of the endoscope.

U.S. Pat. No. 7,914,448 discloses a configuration in which a cooling chamber is formed on a base member where a circuit board is supported, and a heat exchanger is arranged in the cooling chamber. In the this configuration, cooling water circulates inside of the heat exchanger to cool the circuit board where the light source is arranged.

However, in the heat radiating structure of such a cooling water circulation type, it is feared that the cooling water may leak out. In addition, there is a limit in increasing the diameter of the cooling medium tube under the condition that the endoscope should remain narrow. Accordingly, there is a limit in increasing the circulation rate and volume of the cooling water, and consequently, it is unavoidable that the cooling performance is limited.

U.S. Patent Pub. No. 2010-317922 discloses a configuration in which cooling water is circulated to a heat exchanger through a fluid supply channel and a fluid discharge channel, and is controlled using a valve. A light source and an image sensor are arranged adjacent to the heat exchanger to be heat-radiated and cooled according to the circulation of the cooling water.

In the heat radiating structure with the above-mentioned structure, it is unavoidable that the front end portion is increased in size due to the valve arranged therein. In addition, since the fluid supply channel and the fluid discharge channel are separately configured, there are disadvantages in that it is unavoidable that the diameter of the endoscope is increased, and the flexibility of manipulation is deteriorated.

Japanese Patent Pub. No. 2007-007321 discloses a configuration in which an air conduit is arranged between a light source and an image sensor to cool the light source and the image sensor.

The heat radiating structure using the air conduit is limited in increasing the contact area between the cooling medium and a heating element, and if the air conduit is divided into a plurality of branches in order to increase the contact area, there is a problem in that the size of the front end portion of the endoscope is increased.

U.S. Patent Pub. No. 2011-0092772 discloses a configuration in which power is supplied to a light source and heat generated from the light source is transferred using an electric conductor.

However, if the diameter of the electric conductor is increased inside of the endoscope, the flexibility of manipulation is deteriorated. If the diameter of the electric conductor is reduced, the contact area with the light source is reduced, thereby unavoidably reducing the heat conductivity. Even if the heat conductivity is secured by increasing the diameter of the electric conductor while somewhat sacrificing the manipulation flexibility, this will cause the thickness of the front end portion of the endoscope to be increased.

SUMMARY OF THE INVENTION

The present invention has been made to address at least the problems and disadvantages described above and to provide at least the advantages described below. Accordingly, an aspect of the present invention is to provide an endoscope having a heat radiating structure capable of increasing a contact area with a heating element to improve heat conductivity.

Another aspect of the present invention is to provide an endoscope capable of efficiently discharging the heating energy of the front end portion to the outside of the system, and more particularly, to the outside of a human body.

Still another aspect of the present invention is to provide an endoscope configured to be capable of suppressing the increase of the size of the front end portion of the endoscope while efficiently discharging the heating energy of the front end portion.

Yet another aspect of the present invention is to provide an endoscope capable of maintaining flexibility in manipulating the front end portion of the endoscope while efficiently discharging the heating energy of the front end portion.

In accordance with an aspect of the present invention, an endoscope includes a flexible insertion tube; a distal end assembly provided at an end of the insertion tube; and a cooling medium tube provided inside of the insertion tube, and connected to the distal end assembly. A cooling medium for cooling the distal end assembly is introduced through one of the insertion tube and the cooling medium tube, and discharged through the other of the insertion tube and the cooling medium tube.

In accordance with another aspect of the present invention, an endoscope includes a flexible insertion tube; a cooling medium tube provided inside of the insertion tube; a distal end body connected to the insertion tube through a joint assembly; and a light source provided in the distal end body. The cooling medium tube is connected to the distal end body to cool the distal end body and the light source, and a cooling medium for cooling the distal end assembly is introduced through one of the insertion tube and the cooling medium tube, and discharged through the other of the insertion tube and the cooling medium tube.

BRIEF DESCRIPTION OF THE DRAWINGS

The above and other aspects, features, and advantages of the present invention will be more apparent from the following detailed description taken in conjunction with the accompanying drawings, in which.

DETAILED DESCRIPTION OF EMBODIMENTS OF THE PRESENT INVENTION

Figure 1:
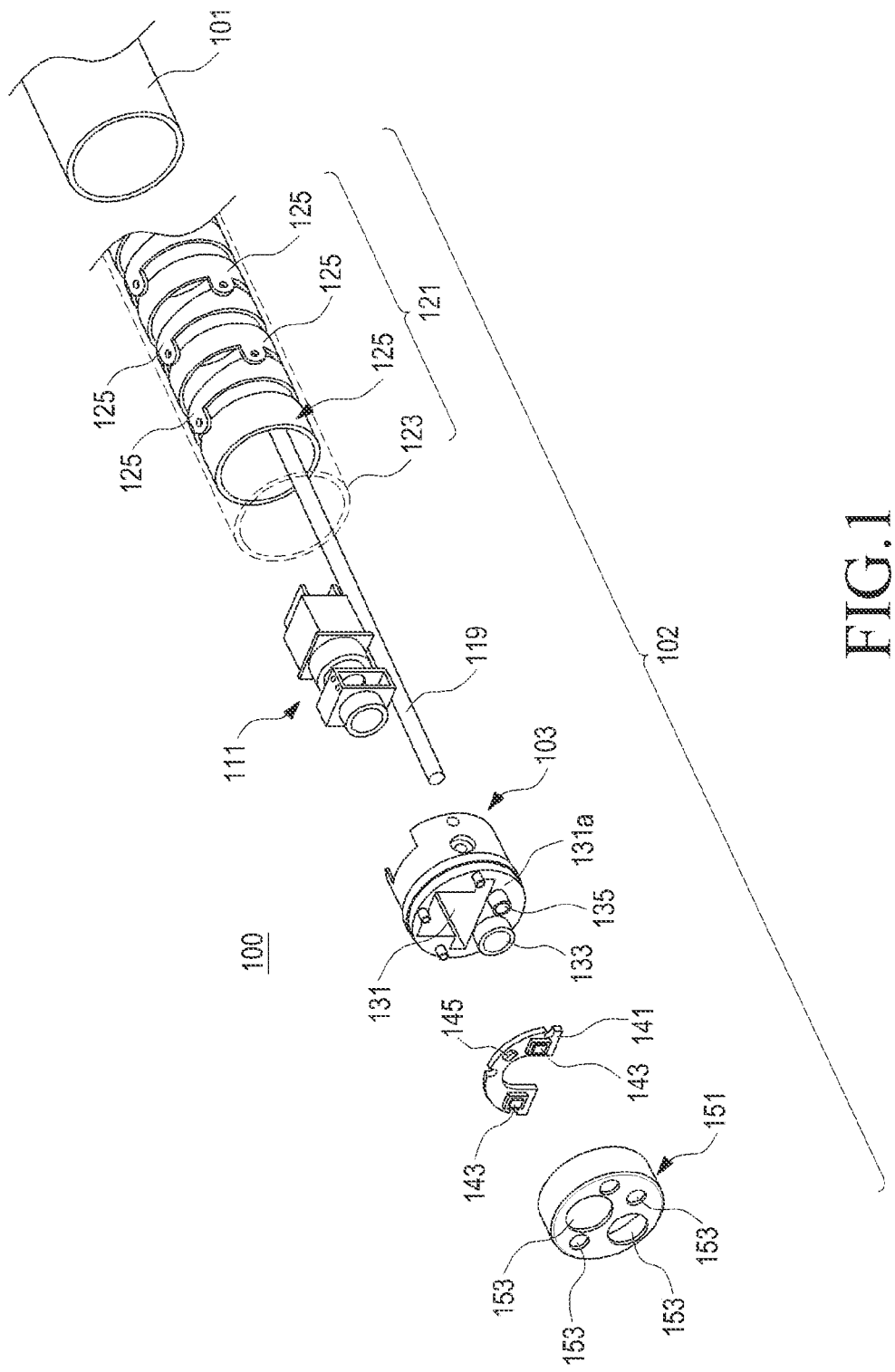
FIG. 1 is an exploded perspective view illustrating an endoscope according to an embodiment of the present invention.

Hereinafter, various embodiments of the present invention will be described with reference to the accompanying drawings. Further, in the following description of the present invention, a detailed description of known functions and configurations incorporated herein will be omitted when it may make the subject matter of the present invention unclear.

As illustrated in FIGS. 1 to 5, the endoscope 100 according to an embodiment of the present invention includes an insertion tube 101, a distal end assembly 102, and a cooling medium tube 119, in which cooling medium cools the distal end assembly 102. The cooling medium for cooling the distal end assembly 102 is introduced through one of the cooling medium tube 119 and an insertion tube 101, and is discharged through the other of the cooling medium tube 119 and the insertion tube 101.

Since the endoscope 100 is inserted into a human body, the endoscope 100 has flexibility such that the endoscope 100 can be moved with respect to a patient's organs. The distal end assembly 102 is coupled to the end of the insertion tube 101, and includes a distal end body 103 where, for example, an image sensor 111 and a light source 143 are mounted, and a joint assembly 121. The joint assembly 121 is deformable and can be curved in various directions by an operator's (i.e. a doctor's) manipulation of an endoscope equipment. The cooling medium tube 119 provides a flow path that is connected to the distal end assembly 102, more specifically, to the distal end body 103 to supply the cooling medium to the distal end body 103, or to discharge the cooling medium around the distal end body 103.

Figure 17:
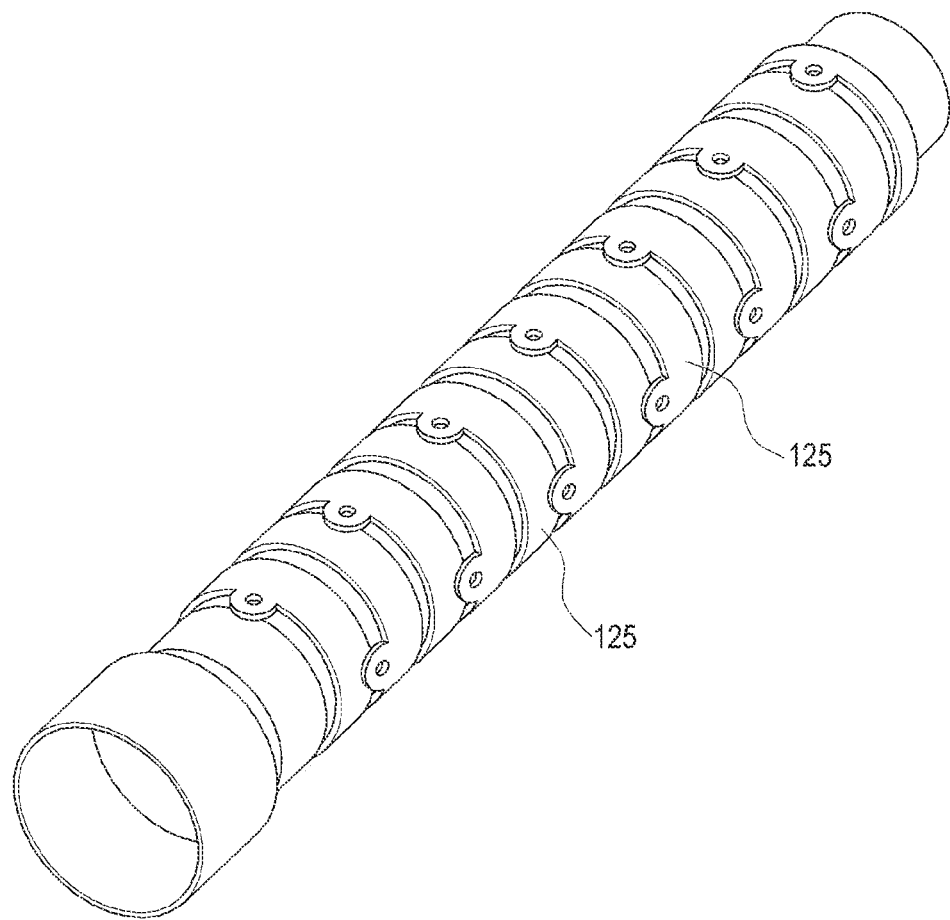
FIG. 17 is a perspective view illustrating a joint assembly of the endoscope illustrated in FIG. 1.

Referring to FIG. 17, the joint assembly 21 is formed by connecting a plurality of joint members 125 serially to be capable of being rotated in relation to each other. According to the rotation of the joint members 125, the joint assembly 121 can be deformed to be curved in various directions. Accordingly, the operator may adjust the progressing direction of the front end portion of the endoscope while inserting the endoscope 100. Although not illustrated, a wire arranged in the inside of the insertion tube 101 is connected to the joint assembly 121, and the operator's manipulation is transmitted to the joint assembly 121 through the wire. Since the joint assembly 121 is inserted inside of a human body, the joint members 125 are preferably wrapped using a protective tube 123. The protective tube 123 prevents the joint member 125 from being contaminated by body fluids or the like, and prevents the joint members 125 from being interfered with an internal organ of the human body. One end of the protective tube 123 is coupled to the insertion tube and the other end is coupled to the distal end body 103. That is, the protective tube 123 provides a sealing structure between the insertion tube 101 and the distal end body 103.

Figure 2:
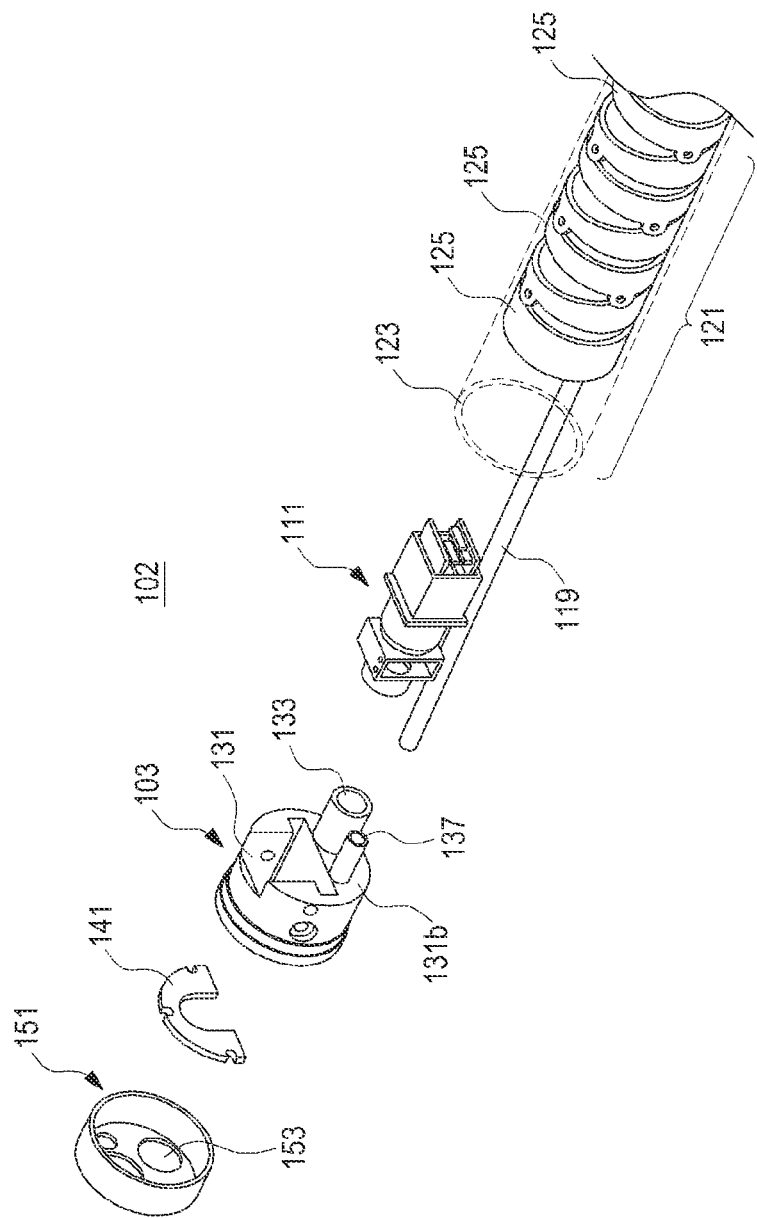
FIG. 2 is an exploded perspective view illustrating the endoscope of FIG. 1 viewed in another direction.
Figure 6:
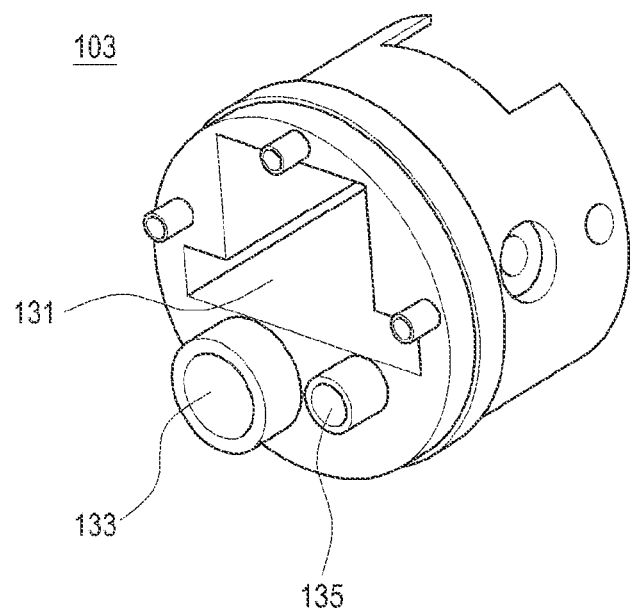
FIG. 6 is a perspective view illustrating the distal end body of the endoscope illustrated in FIG. 1.
Figure 7:
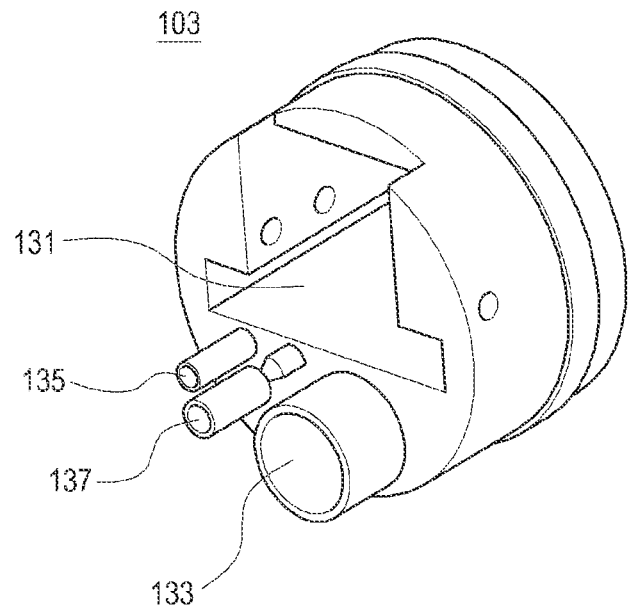
FIG. 7 is a perspective view illustrating the front end portion of the endoscope illustrated in FIG. 6 viewed in another direction.

The distal end body 103 is coupled to an end of the joint assembly 121, more specifically, the one end of the protective tube 123, and provides a space for mounting the image sensor 111 and the light source 143. Referring to FIGS. 6 and 7, the distal end body 103 includes an accommodating hole 131, a treatment hole 133 and a nozzle 135 which extend longitudinally through the distal end body 103. In addition, the distal end body 103 includes a cooling port 137 formed in the rear side 131b, as shown in FIG. 2. The accommodating hole 131 accommodates the image sensor 111, and the treatment hole 133 and the nozzle 135 provide a means for arranging an operating knife and supplying an antiseptic solution or the like in the front side when performing an operation using the endoscope 100.

Figure 3:
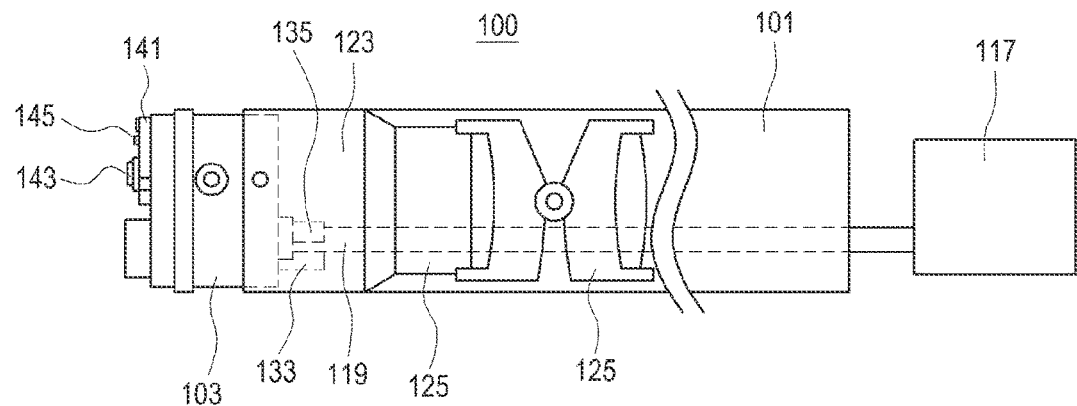
FIG. 3 is a side view illustrating the endoscope of FIG. 1 in the assembled state.
Figure 4:
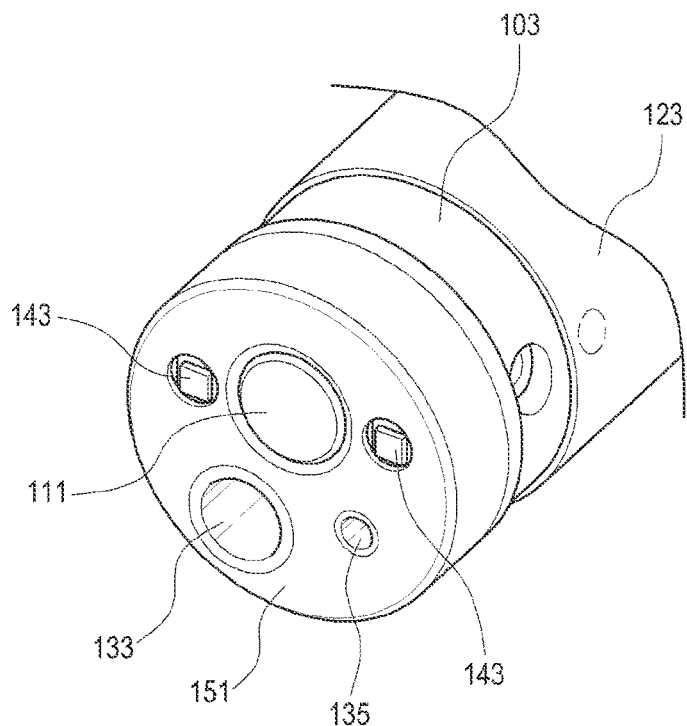
FIG. 4 is a perspective view illustrating the front end portion of the endoscope illustrated in FIG. 3.
Figure 5:
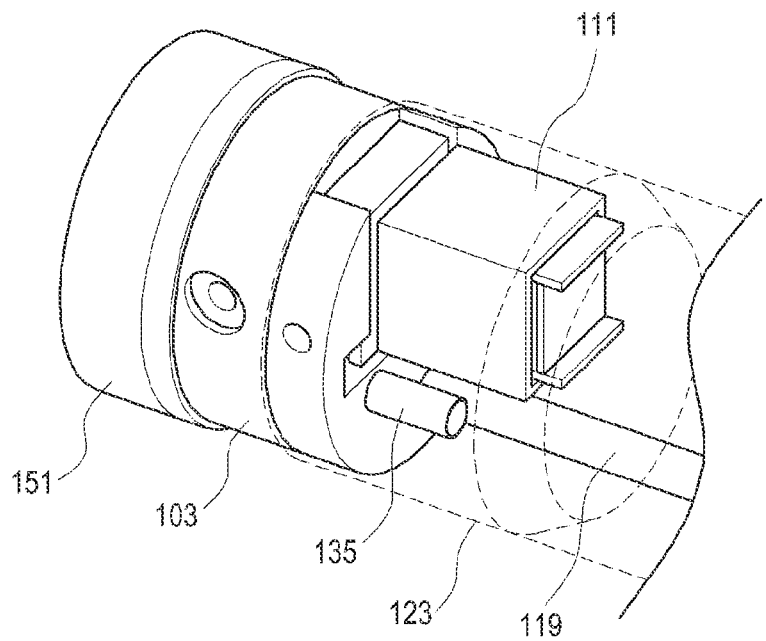
FIG. 5 is a perspective view illustrating the front end portion of the endoscope illustrated in FIG. 4 viewed in another direction.
Figure 8:
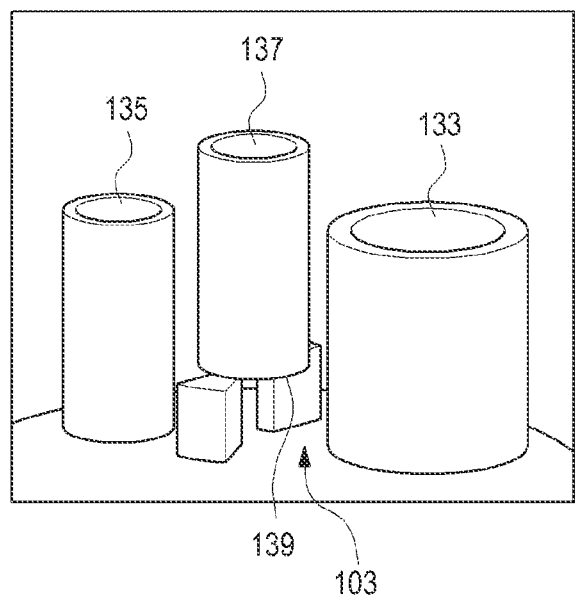
FIG. 8 is a perspective view illustrating a cooling port provided in the distal end body illustrated in FIG. 7.

The cooling port 137 is connected to the cooling medium tube 119. As indicated by reference numeral "139" in FIG. 8, the area between the cooling port and the rear side 131b of the distal end body 103 is at least partly opened such that the cooling medium introduced through the cooling medium tube 119 is injected to the surrounding environment of the distal end body 103. If the cooling medium tube 119 is designed to discharge the cooling medium, the cooling medium introduced through the insertion tube 101 conducts heat exchange between the light source 143 and the distal end body 103, and then is discharged through the cooling medium tube 119. This is enabled by an air pump 117 located outside of the human body and outside of the insertion tube 101 as illustrated in FIG. 3, and connected to the cooling medium tube 119. As the air pump 117 is operated, the cooling medium, for example, external air, is introduced into the front end portion of the endoscope through the cooling medium tube 119, or is discharged from the front end portion of the endoscope 100 after having performed heat exchange. If the cooling medium tube 119 connected with the air pump 117 is configured to discharge the cooling medium, a vacuum pump may be practically used as the air pump 117.

Figure 9:
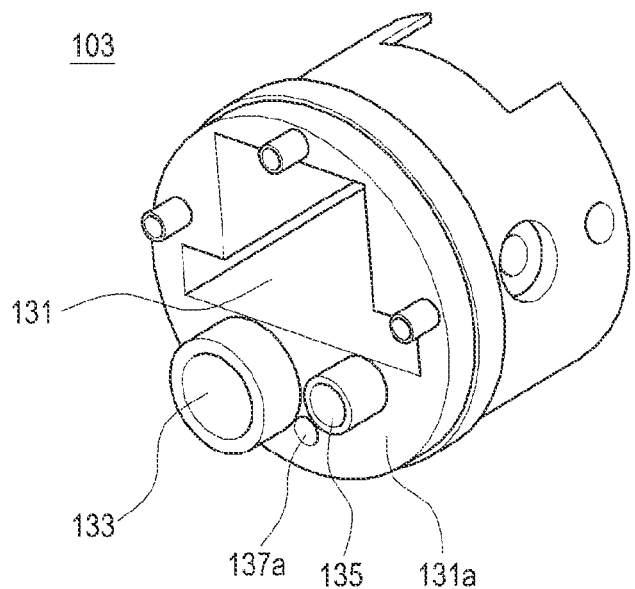
FIG. 9 is a perspective view illustrating a modified embodiment of the distal end body illustrated in FIG. 6.
Figure 10:
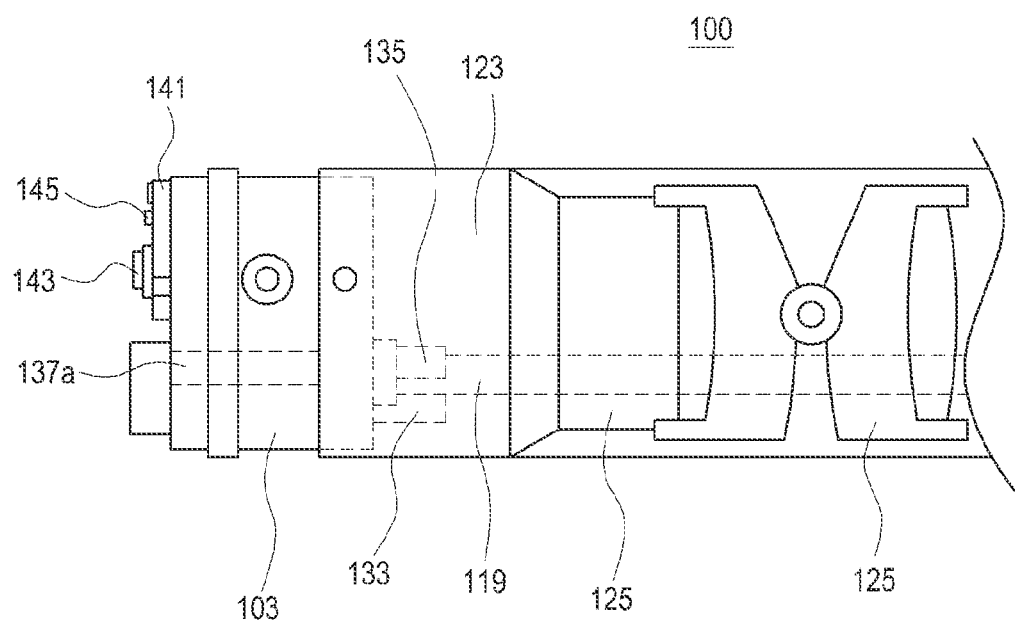
FIG. 10 is a side view illustrating an endoscope provided with the distal end body illustrated in FIG. 9.

As illustrated in FIGS. 9 and 10, the flow path 137a of the cooling port 137 may extend to the front side 131a of the distal end body 103. In such a case, the cooling medium may be supplied to the front side 131a of the distal end body 103, or discharged from the front side 131a of the distal end body 103 to the outside sequentially through the flow path 137a, the cooling port 137 and the cooling medium tube 119 after having performed heat exchange.

Consequently, the cooling medium conducts heat exchange with the front side 131a and rear side 131b of the distal end body 103, and with the entire surface of the distal end body 103 that it may come into contact within the endoscope 100, up to the inner wall of the accommodating hole 131. In addition, the light source 143 is arranged on the distal end body 103, in which the cooling medium arrives at the front side 131a of the distal end body 103 through the accommodating hole 131 or the flow path 137a thereby conducting heat exchange directly with the light source 143.

Figure 11:
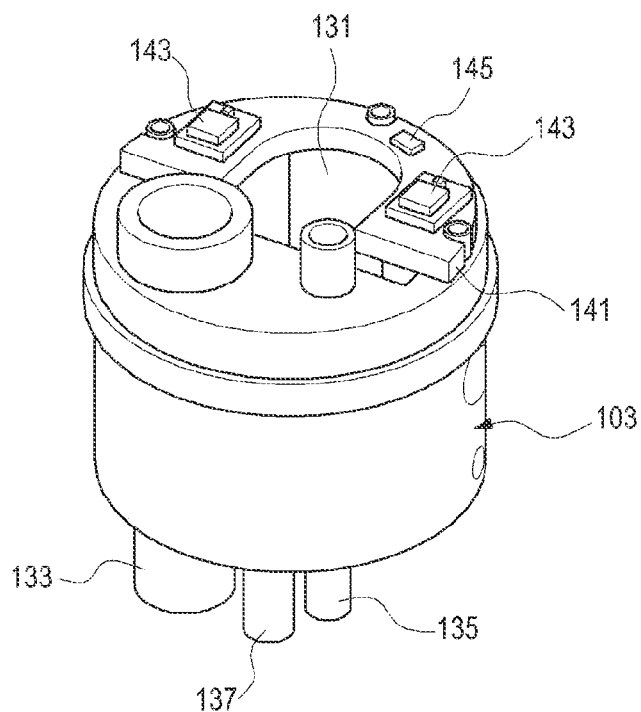
FIG. 11 is a perspective view illustrating the distal end body in a state where a printed circuit board is mounted on the distal end body illustrated in FIG. 1.

As described above, the image sensor 111 is accommodated in the accommodating hole 131. Referring to FIG. 11, the light source 143 is arranged on the distal end body 103, more specifically, on the front side 131a of the distal end body 103 in the state where it is mounted on a separate printed circuit board 141. The printed circuit board 141 may be fabricated from a metallic material, for example, an aluminum material to conduct the heat generated from the light source to the distal end body 103. The distal end body 103 may also be fabricated from a metallic material, for example, an aluminum material to conduct the heat transferred from the light source 143 toward the rear side 131b.

The light source may be arranged on each side of the image sensor 111 on the front side 131a of the distal end body 103. In addition, the printed circuit board 141 may be formed as a flexible printed circuit board. Due to the characteristics of the material, the flexible printed circuit board has a heat conductivity coefficient lower than that of a metallic material board. However, since the thickness of the flexible board is thin as compared to the metallic material board, the flexible board may provide a similar heat conductivity. That is, because the distance between the light source 143 and the distal end body 103 is reduced, a sufficient heat conductivity can be secured even if the heat conductivity coefficient of the flexible printed circuit board is somewhat low.

The printed circuit board 141 may be further equipped with a temperature sensor 145. The temperature sensor 145 detects the internal temperature of the endoscope 100, in particular, the variation of temperature according to the operation of the light source 143. When the temperature sensor 145 detects the increase of internal temperature of the endoscope 100 to a level that may cause damage to an organ of the human body, the endoscope equipment generates an alarm signal or controls the air pump 117 to increase the flow rate of the cooling medium. When the temperature sensor 145 senses that the internal temperature of the endoscope is in a safe range, the endoscope equipment again controls the air pump 117 to reduce the flow rate of the cooling medium.

The distal end body 103 is provided with a cap member 151 to protect the printed circuit board 141, the light source 143, and the image sensor 111. That is, the cap member 151 prevents the printed circuit board 141 or the like from being contaminated by body fluids or the like inside of the human body. However, the cap member 151 may be formed with a plurality of openings 153 in order to provide a photographing path of the image sensor 111, a path for providing the illumination of the light source 143, or a path in which the treatment hole 133 and the nozzle 135 are arranged.

A temperature distribution was measured for the inventive endoscope and a conventional endoscope when the light source was operated, in which in the inventive endoscope, the distal end body was fabricated from a metallic material, and the printed circuit board on which the light source was mounted was also fabricated from a metallic material, and in the conventional endoscope, the printed circuit board was fabricated from a conventional dielectric substrate. In the case of the inventive endoscope, it was confirmed that when the light source is operated, the highest temperature at the front end portion, more particularly at the light source, was about 68.11° C., the temperature distribution of the endoscope is gradually reduced as being spaced far away from the front end portion and approaches room temperature. When the light source was arranged on the dielectric substrate and then mounted on the distal end body, the highest temperature of the front end portion arrived at about 542.7° C. Furthermore, the endoscope, in which the light source was arranged on the dielectric substrate and then mounted on the distal end body, showed a temperature distribution in which the temperature approaches room temperature from the rear side of the dielectric substrate, i.e., the distal end body. Consequently, that is, when a conventional printed circuit board is used, the heat generated from the light source is concentrated only on the light source rather than being diffused. As described above, when the heat is concentrated only on the light source, an organ of the human body may be damaged due to the excessively high temperature.

Figure 12:
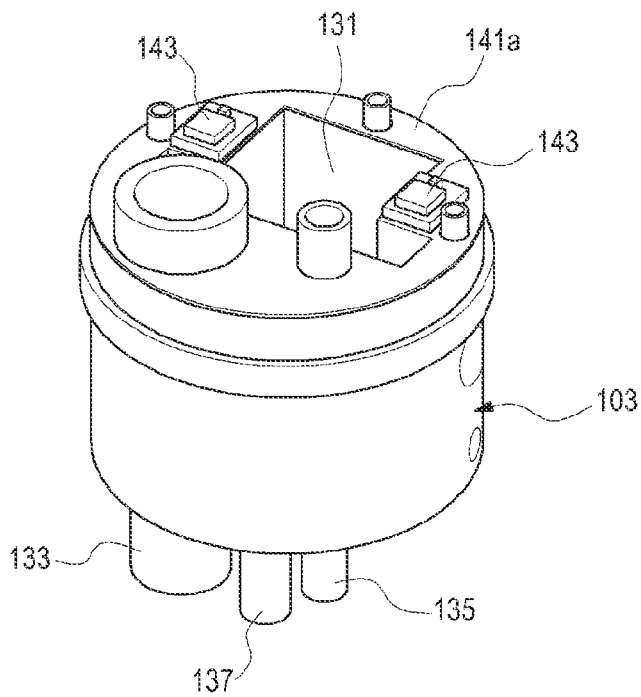
FIG. 12 is a perspective view illustrating the distal end body in a state where a light source is mounted on the distal end body illustrated in FIG. 11.
Figure 13:
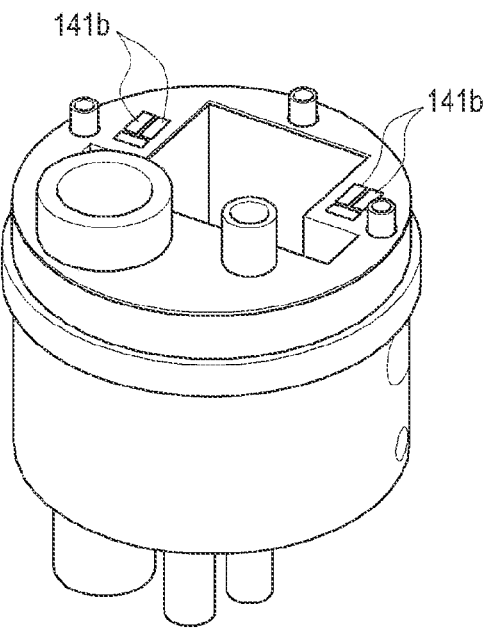
FIG. 13 is a perspective view illustrating the distal end body in a state where a printed circuit pattern is provided on the distal end body in order to mount the light source illustrated in FIG. 12.

Meanwhile, as illustrated in FIGS. 12 and 13, the light source 143 may be directly mounted on the front side 131a of the distal end body 103. However, since the distal end body 103 is also fabricated from a metallic material, the front side a of the distal end body 103 is preferably coated with an insulation material, for example, a ceramic material. Electrodes 141b connected to the light source 143 may be provided by forming a printed circuit pattern on a coating layer 141a formed from an insulation material. The coating layer 141a formed from the insulation material may reduce the space between the light source 143 and the distal end body to increase the heat conductivity like the flexible printed circuit board. In addition, if the coating layer 141a is formed from a ceramic material, it is possible to increase the heat conductivity since the heat conductivity coefficient of the ceramic material is higher than that of the flexible printed circuit board.

Figure 14:
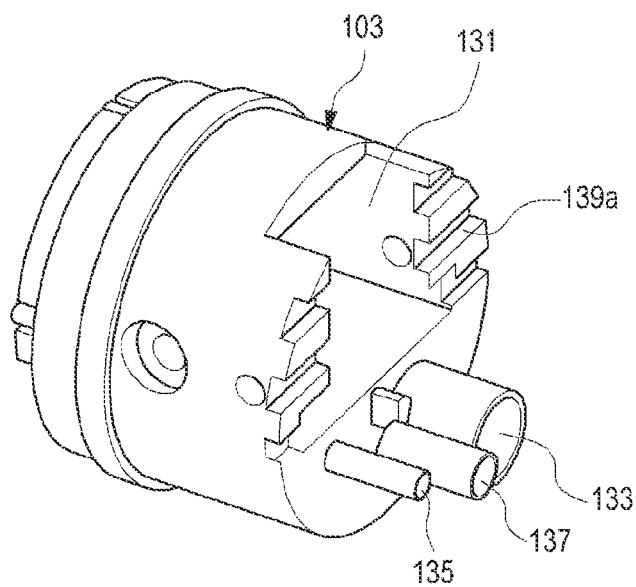
FIGS. 14 to 16 are perspective views illustrating the distal end body in a state in which heat radiating fins are formed on the distal end body illustrated in FIG. 6.
Figure 15:
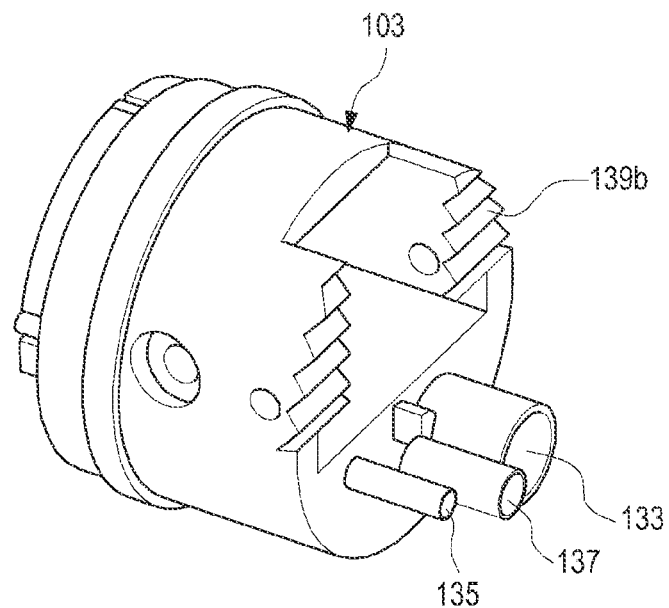
Figure 16:
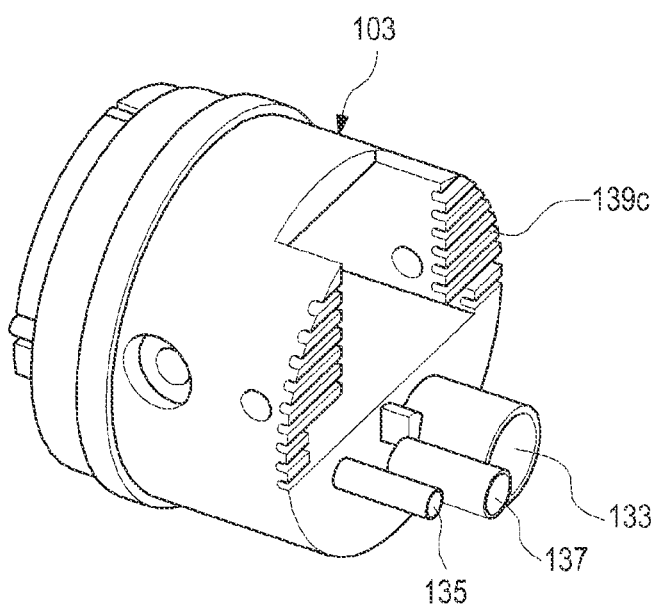

In addition, if the distal end body 103 and the light source 143 are contacted with the cooling medium over a wider area, the heat conductivity, in other words, the heat radiating and cooling effects, can be further increased. FIGS. 14 to 16 illustrate configurations in which heat radiating fins are formed on the distal end body 103 in order to increase the contact area of the distal end body 103 with the cooling medium. The heat radiating fins illustrated in each of the drawings are configured to have rectangular grooves 139a, V-shaped grooves 139b, or U-shaped grooves 139c arranged between the fins, respectively. By forming the heat radiating fins, the distal end body 103 is contacted with the cooling medium over a wider area to conduct the heat exchange, as described above. It is obvious that the height of the heat radiating fins is increased within a range allowed by the internal space of the front end portion of the endoscope 100, and in a range where the endoscope 100 is manipulated without interference, the heat conductivity can be further increased.

TABLE 1

| Type | | Temperature of light source (° C.) | Temperature of rear side of the distal end body (° C.) |
|---|---|---|---|
| Invention | Before cooling | 52.5 | 27 |
| | After cooling | 28.1 | 25.4 |
| Structure 1 | Electric conductor conducting type | Before cooling | 63 | 28.7 |
| | After cooling | 56 | 30 |
| Structure 2 | Cooling water introducing and discharging channel type | Before cooling | 52.1 | 26.7 |
| | After cooling | 38.9 | 25.3 |
| Structure 3 | Air introducing and discharging channel type | Before cooling | 52.3 | 27.4 |
| | After cooling | 39.8 | 25.5 |

Table 1 represents the results obtained by measuring temperature distributions according to the operation of different heat radiating structures under the conditions where the arrangements of front end bodies, light sources, etc. are the same. The measurement of the temperature distributions was performed under the condition where room temperature is 25° C. and the relative humidity is 60%.

In Table 1, the structure 1 used the electric conductor connected to the light source as a heat radiating and cooling structure, the structures 2 and 3 separately arrange a flow path for introducing cooling medium, and a flow path for discharging, in which the structure 2 uses a cooling water as the cooling medium and the structure uses air as the cooling medium. As indicated in Table 1, the temperatures of the light sources prior to cooling are similar to each other in all the structures. However, after cooling, that is, when the cooling medium is introduced and circulated, the endoscope 100 configured in accordance with the present invention was capable of remaining close to room temperature of the above-mentioned measuring condition of the light source 143 unlike the other structures.

As described above, the inventive endoscope is configured such that a light source is arranged in the front end portion thereof, and a cooling medium, i.e., external air, can be forcibly circulated inside the front end portion, in particular, around a distal end body which is equipped with the light source and around the light source. Accordingly, it can contribute to improve the heat radiating and cooling effects of the light source. In addition, the heat generated from the light source is transferred to a structure around the light source, in particular, to the distal end body, and the cooling medium directly conducts heat exchange while being circulated around the distal end body and the light source which is a heating element, thereby enhancing the heat radiating and cooling effects.

Furthermore, since the inventive endoscope uses the insertion tube of the endoscope itself as a medium flow path for supplying or discharging the cooling medium, there is an advantage in that it is easy to reduce the diameter of the endoscope. Moreover, as compared to a conventional structure in which a flow path for supplying the cooling medium and a flow path for discharging the cooling medium are separatedly arranged, the inventive endoscope is improved in manipulation flexibility that is required for a change of direction.

While the present invention has been shown and described with reference to certain embodiments thereof, it will apparent to those skilled in the art that various changes in form and details may be made therein without departing from the spirit and scope of the present invention as defined by the appended claims.

What is claimed is:
1. An endoscope, comprising:
   a flexible insertion tube;
   a distal end assembly including a distal end body provided at an end of the insertion tube, a cooling port formed in a rear side of the distal end body, at least one heat radiating fin on a rear side of the distal end body, and a joint assembly configured to connect the distal end body to the insertion tube; and
   a single cooling medium tube provided inside of the insertion tube, and connected to the cooling port to supply the cooling medium around the distal end body, or to discharge the cooling medium after having conducted heat exchange with the distal end body,
   wherein a space between the distal end body and the cooling port is partly opened, and
   wherein one of the insertion tube itself and the single cooling medium tube is configured to introduce a cooling medium for cooling the distal end body and to circulate the cooling medium around the distal end body, and the other of the insertion tube itself and the single cooling medium tube is configured to discharge the cooling medium from the distal end body after the cooling medium is circulated around the distal end body.

2. The endoscope of claim 1, further comprising an air pump connected to the single cooling medium tube,
   wherein when the air pump is operated, external air is introduced to the distal end assembly or the air circulated around the distal end assembly is discharged through the single cooling medium tube.

3. The endoscope of claim 1, wherein the distal end assembly further comprises a protective tube configured to wrap the joint assembly.

4. The endoscope of claim 1, wherein the cooling port is connected to a front side of the distal end body through the distal end body such that the cooling medium is supplied to the front side of the distal end body.

5. The endoscope of claim 1, wherein the distal end assembly comprises a light source provided in the distal end body, and
wherein heat generated from the light source is transferred to the distal end body, and the cooling medium supplied through the single cooling medium tube or the insertion tube itself conducts heat exchange with the light source and the distal end body.

6. The endoscope of claim 5, wherein the distal end assembly further comprises a printed circuit board mounted on a front side of the distal end body, and
wherein the light source is mounted on the printed circuit board.

7. The endoscope of claim 6, wherein the printed circuit board is formed from a metallic material or is a flexible printed circuit board.

8. The endoscope of claim 5, wherein the distal end assembly further comprises an insulation layer formed on a front side of the distal end body, and a printed circuit pattern formed on the insulation layer, and
wherein the light source is mounted on the printed circuit pattern.

9. The endoscope of claim 5, wherein the distal end assembly further comprises a temperature sensor mounted on the distal end body.

10. The endoscope of claim 5, wherein the distal end assembly further comprises an image sensor mounted on a front side of the distal end body, and
wherein a plurality of the light sources are arranged around the image sensor on the front side of the distal end body.

11. The endoscope of claim 10, wherein the distal end assembly further comprises an accommodating hole formed through the distal end body along a longitudinal direction of the distal end assembly, and
wherein the image sensor is mounted in the accommodating hole.

12. An endoscope, comprising:
a flexible insertion tube;
a single cooling medium tube provided inside of the insertion tube;
a distal end body connected to the insertion tube through a joint assembly;
at least one heat radiating fin on a rear side of the distal end body;
a cooling port formed in the rear side of the distal end body; and
a light source provided in the distal end body,
wherein a space between the distal end body and the cooling port is partly opened
wherein the single cooling medium tube is connected to the cooling port to cool the distal end body and the light source, and one of the insertion tube itself and the single cooling medium tube is configured to introduce a cooling medium for cooling the distal end body and the light source and to circulate the cooling medium around the distal end body and the light source, and the other of the insertion tube itself and the single cooling medium tube is configured to discharge the cooling medium from the distal end assembly after the cooling medium is circulated around the distal end body, and
wherein the single cooling medium tube is connected to the cooling port to supply the cooling medium around the distal end body or to discharge the cooling medium after having conducted heat exchange with the distal end body.

13. The endoscope of claim 12, wherein the distal end body is formed from an aluminum material, and heat generated from the light source is transferred through the distal end body.

14. The endoscope of claim 12, further comprising a printed circuit board arranged on a front side of the distal end body,
wherein the printed circuit board is formed from a metallic material or is a flexible printed circuit board, and the light source is arranged on the printed circuit board.

* * * * *